United States Patent [19]

Gao et al.

[11] Patent Number: 5,795,587
[45] Date of Patent: Aug. 18, 1998

[54] STABLE LIPID-COMPRISING DRUG DELIVERY COMPLEXES AND METHODS FOR THEIR PRODUCTION

[75] Inventors: Xiang Gao, Pittsburgh; Leaf Huang, Wexford, both of Pa.

[73] Assignee: University of Pittsburgh, Pittsburgh, Pa.

[21] Appl. No.: 376,701

[22] Filed: Jan. 23, 1995

[51] Int. Cl.$^6$ .................................................. A61K 9/127
[52] U.S. Cl. ............................................ 424/450; 935/54
[58] Field of Search .......................... 424/450; 935/54; 264/4.1, 4.3

[56] References Cited

U.S. PATENT DOCUMENTS

| | | | |
|---|---|---|---|
| 4,544,545 | 10/1985 | Ryan et al. | 424/1.1 |
| 4,897,355 | 1/1990 | Eppstein et al. | 435/240.1 |
| 4,958,013 | 9/1990 | Letsinger | 536/27 |
| 5,100,662 | 3/1992 | Bolcsak et al. | 424/88 |
| 5,264,618 | 11/1993 | Felgner et al. | 560/224 |
| 5,279,833 | 1/1994 | Rose | 424/450 |
| 5,283,185 | 2/1994 | Epand et al. | 435/172.3 |
| 5,334,761 | 8/1994 | Gebeyehu et al. | 564/197 |
| 5,366,737 | 11/1994 | Eppstein et al. | 424/450 |
| 5,374,548 | 12/1994 | Carer | 424/450 |
| 5,540,933 | 7/1996 | Ruoslahti | 424/450 |

OTHER PUBLICATIONS

Robert L. Letsinger, et al., "Cholesteryl–Conjugated Oligonucleotides: Synthesis, Properties, and Activity as Inhibitors of Replication of Human Immunodeficiency Virus in Cell Culture", (Sep. 1989), Proc. Natl. Acad. Sci. USA, vol. 86:6553–6556.
James J. Cheetham, et al., "Cholesterol Sulfate Inhibits the Fusion of Sendai Virus to Biological and Model Membranes", (1990), Journal of Biological Chemistry, vol. 265:12404–12409.
John K. Rose, et al., "A New Cationic Liposome Reagent Mediating Nearly Quantitative Transfection of Animal Cells", (Apr. 1991), BioTechniques, vol. 10:520–525.
Leonidas Stamatatos, et al., "Interactions of Cationic Lipid Vesicles with Negatively Charged Phospholipid Vesicles and Biological Membranes", (1988), Biochemistry, vol. 27:3917–3925.
Philip L. Felgner, "Lipofection: A Highly Efficient, Lipid–Mediated DNA–Transfection Procedure", (Nov. 1987), Proc. Natl. Acad. Sci. USA, vol. 84:7413–7417.
J. P. Behr et al., "Efficient Gene Transfer Into Mammalian Primary Endocrine Cells with Lipopolyamine–Coated DNA", (Sep. 1989), Proceedings of the National Academy of Sciences of USA, vol. 86:6982–6986.
K. M. Hui, et al., "Induction of Alloreactive Cytotoxic T Lymphocytes by Intrasplenic Immunization with Allogenic Class I Major Histocompatibility Complex DNA and DC–CHOL Cationic Liposomes" (Nov. 1994), Journal of Liposome Research, vol. 4:1077–1078.
M. J. Stewart, et al., "Gene Transfer In Vivo with DNA–Liposome Complexes:Safety and Acute Toxicity in Mice" (Jun. 1992), Human Gene Therapy, vol. 3:267–275.
B. A. Demeneix, "Temporal and Spatial Expression of Lipospermine–Compacted Genes Transferred Into Chick Embryos In Vivo", (Mar. 1994), BioTechniques, vol. 16:496–501.
Zhou, BBA 1065 (1991) pp. 8–14.
Malone, PNAS 86, p. 6077, 1989.
Gao, BBRC 179, #1, p. 280, 1991.
Pinnaduwage BBA, 985, p. 33, 1989.
Sternberg in FEBS Letters 356 (1994) p. 361.

Primary Examiner—Gollamudi S. Kishore
Attorney, Agent, or Firm—Morgan & Finnegan, LLP

[57] ABSTRACT

Novel stable, concentrated, biologically active and ready-to-use lipid-comprising drug delivery complexes and methods for their production are described. The biological activity of the complexes produced are comparable to the formulations prepared according to the prior art admixture method and upon purification, the complexes produced by the method of this invention are 50 to 500 fold more concentrated than the components of the complexes formed by admixture. The method described herein provides for the large scale production of lipid-comprising drug delivery systems useful for gene therapy and other applications.

21 Claims, 6 Drawing Sheets

STABLE LIPID-COMPRISING DRUG DELIVERY COMPLEXES AND METHODS FOR THEIR PRODUCTION

FIELD OF INVENTION

The present invention relates to cationic lipids and their use as vehicles for the transfer of nucleic acids or other macromolecules such as proteins into cells. More specifically, this invention relates to lipid-comprising drug delivery complexes which are stable, biologically active, capable of being concentrated, and to methods for their production.

BACKGROUND OF INVENTION

The development of new forms of therapeutics which use macromolecules such as proteins or nucleic acids as therapeutic agents has created a need to develop new and effective means of delivering such macromolecules to their appropriate cellular targets. Therapeutics based on either the use of specific polypeptide growth factors or specific genes to replace or supplement absent or defective genes are examples of therapeutics which may require such new delivery systems. Clinical application of such therapies depends not only on efficacy of new delivery systems but also on their safety and on the ease with which the technologies underlying these systems can be adapted for large scale pharmaceutical production, storage, and distribution of the therapeutic formulations. Gene therapy has become an increasingly important mode of treating various genetic disorders. The potential for providing effective treatments, and even cures, has stimulated an intense effort to apply this technology to diseases for which there have been no effective treatments. Recent progress in this area has indicated that gene therapy may have a significant impact not only on the treatment of single gene disorders, but also on other more complex diseases such as cancer. However, a significant obstacle in the attainment of efficient gene therapy has been the difficulty of designing new and effective means of delivering therapeutic nucleic acids to cell targets. Thus, an ideal vehicle for the delivery of exogenous genes into cells and tissues should be highly efficient in nucleic acid delivery, safe to use, easy to produce in large quantity and have sufficient stability to be practicable as a pharmaceutical.

Non-viral vehicles, which are represented mainly by the cationic liposomes, are one type of vehicle which have, for the following reasons, been considered for use in gene therapy. First, the plasmid DNA required for liposome-mediated gene therapy can be widely and routinely prepared on a large scale and is simpler and carries less risk than the use of viral vectors such as retroviruses. Second, liposome-mediated gene delivery, unlike retroviral-mediated gene delivery, can deliver either RNA or DNA. Thus, DNA, RNA, or an oligonucleotide can be introduced directly into the cell. Moreover, cationic liposomes are non-toxic, non-immunogenic and can therefore be used repeatedly in vivo as evidenced by the successful in vivo delivery of genes to catheterized blood vessels (Nabel, E. G., et al. (1990) *Science,* 249: 1285–1288), lung epithelial cells (Brigham, K. L., et al. (1989) *Am. J. Respir. Cell Mol. Biol.,* 195–200, Stribling, R., et al. (1992) *Proc. Natl. Acad. Sci. U.S.A.,* 89: 11277–11281), and other systemic uses (Zhu, N., et al. (1993) *Science,* 261: 209–211, Philip, R., et al. (1993) *Science,* 261: 209–211) of cationic liposomes.

Although a variety of cationic liposome formulations, including the commercially available cationic liposome reagent DOTMA/DOPE (N-[1,-(2,3-dioleoyloxy)propyl]-N, N,N-trimethyl ammonium chloride/dioleoyl phosphatidylethanolamine), are known in the art (Felgner, P. L. et al. (1987) *Proc. Natl. Acad. Sci. U.S.A.,* 84: 7413–7417), a cationic liposome formulation designated DC-Chol/DOPE (3β[N-(N',N'-dimethylaminoethane)-carbamoyl] cholesterol)/(dioleoyl phosphatidylethanolamine)) has been shown in in vitro studies (Gao, X., and Huang, L. (1991) *Biochem. Biophys. Res. Commun.,* 179: 280–285) to be relatively non-toxic and more efficient than DOTMA/DOPE. Moreover, following extensive in vivo studies (Plautz, G. E., et al. (1993) *Proc. Natl. Acad. Sci. U.S.A.,* 90: 4645–4649, Stewart, M. J., et al. (1992) *Hum. Gene Ther.,* 3: 267–275) in which DC-Chol/DOPE was demonstrated to be both safe and efficacious as a nucleic acid delivery system, this formulation was approved by the U.S. Food and Drug Administration (FDA) and the U.K. Medicines Control Agency (MCA), and has been used in two separate gene therapy clinical trials (Nabel, G. J., et al. (1993) *Proc. Natl. Acad. Sci. U.S.A.,* 90: 11307–11311, Caplen, N. J., et al. (1995) *Nature Medicine,* 1:39–46).

However, the use of DC-Chol/DOPE and other currently existing cationic liposomes as vehicles for delivering nucleic acids to cellular targets are inconvenient for large scale therapeutic applications for a number of reasons. First, the ratios of liposome to nucleic acid utilized to form nucleic acid/liposome complex in the prior art admixture method results in the formation of complexes which are large in diameter and hence, relatively low in stability. Thus, none of the presently utilized cationic liposome formulations, including DC-Chol/DOPE, are designed as stable and ready-to-use pharmaceutical formulations of nucleic acid/liposome complex. This limitation of the admixture method requires that the user prepare complex prior to each use, an inconvenience which requires special training of personnel. In addition, the preparation of complex by admixture prior to each use introduces a possible source of dosage variability which hinders evaluation of treatments utilizing these complexes due to possible over- or under-dosing of the recipient.

Second, the prior art admixture method of preparing nucleic acid/cationic liposome complexes prior to each use requires that a dilute nucleic acid solution (less than 4 µg/ml) and a dilute liposome dispersion (less than 50 µM) be used to prepare the nucleic acid/liposome complex in order to reduce the chance of forming large and less active aggregates. This limitation makes it difficult to make small biologically active complexes without using less than optimal conditions, such as reducing the amount of liposomes (which causes reduced nucleic acid transfer activity) or increasing the amount of liposome (which causes enhanced toxicity). Moreover, the fact that the complex must be made in dilute concentrations is a significant drawback to clinical applications, particularly in the case of intratumor injection of the complex, since only a small volume of the complex can be injected in each site (Nabel, G. J., et al. (1993) *Proc. Natl. Acad. Sci. U.S.A.,* 90: 11307–11311).

Accordingly, an object of this invention is to provide stable, biologically active, lipid-comprising drug delivery complexes which are capable of being concentrated as well as methods of producing such complexes.

SUMMARY OF INVENTION

This invention provides methods for producing lipid-comprising drug delivery complexes having a net positive charge at pH 6.0–8.0. By "drug" as used throughout the specification and claims is meant any molecular entity, which is either monomeric or oligomeric, and which, when complexed with lipid or with lipid and polycation, is being administered to an individual for the purpose of providing a therapeutic effect to the recipient. Thus, macromolecules having an overall net negative charge or regions of negativity would be expected to be capable of forming the delivery complexes of this invention. Macromolecules which are particularly suitable for use with the complexes of this invention are for example, DNA, RNA, oligonucleotides or negatively charged proteins. However, macromolecules having a positive charge (eg large cationic protein would also be expected to be capable of forming the complexes of this invention by sequentially complexing the cationic macromolecule with anionic lipid or polymer and then with cationic lipid.

The complexes of the present invention comprise a drug/lipid complex formed by mixing the drug to be delivered with cationic liposomes in a drug to lipid ratio such that the drug/lipid complex formed has a net positive charge and a drug/lipid/polycation complex formed by mixing drug with cationic liposomes and polycation in a drug to lipid to polycation ratio such that the drug/lipid/polycation complex formed has a net positive charge. By "net positive charge" as applied to the drug/lipid complex is meant a positive charge excess of lipid to DNA. By "net positive charge" as applied to the drug/lipid/polycation complex is meant that the positive charges of the cationic lipid and the polycation exceed the negative charge of the drug.

The invention therefore relates to methods for producing these drug/lipid and drug/lipid/polycation complexes comprising mixing the drug to be delivered with cationic liposomes, and optionally polycation, in a ratio such that the complex formed has a net positive charge.

In another embodiment of this invention, the methods for producing drug lipid or drug/lipid/polycation complexes may further comprise the step of purifying said complexes from excess free components (drug, lipid, polycation) following their production.

The drug/lipid and drug/lipid/polycation complexes of this invention are generally stable, capable of being produced at relatively high concentration, and retain biological activity over time in storage. Such complexes are of utility in the delivery of nucleic acids, proteins and other macromolecules to cells and tissues.

A BRIEF DESCRIPTION OF THE DRAWINGS

FIGS. 2A and 2B is indicated at the top of FIG. 2A.

Figure 2A:
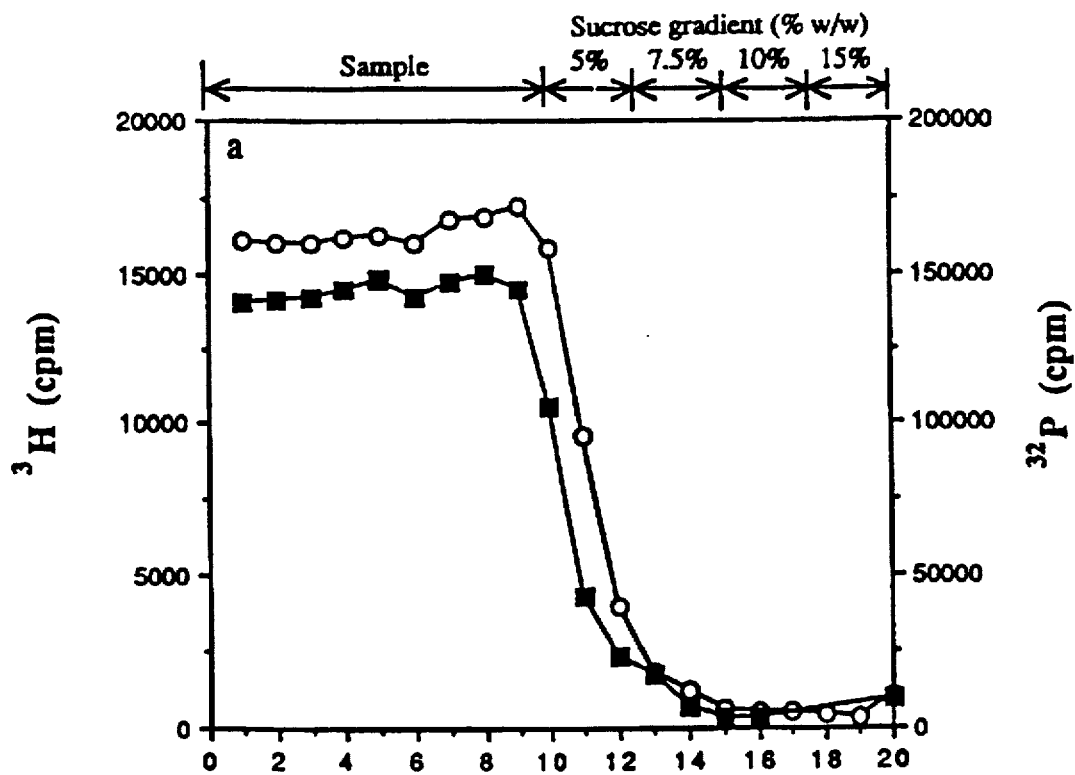
FIGS. 2A and 2B show the distribution of the liposome marker $^3$H-cholesteryl hexadecyl ether (○) and the $^{32}$P-DNA marker (■) among sucrose gradient fractions. The location of each fraction in the sucrose gradients of both
Figure 2B:
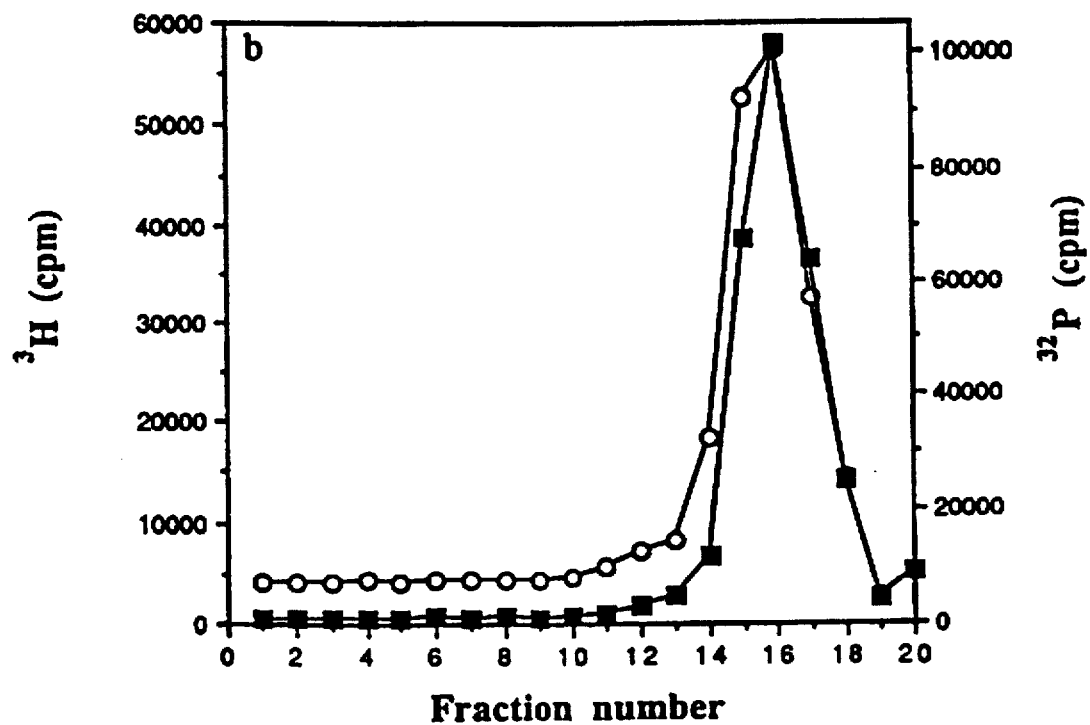

FIG. 2A shows the distribution of the $^3$H and $^{32}$P markers following ultracentrifugation of free liposomes (10 μmoles of DC-Chol/DOPE (2:3) in 2 ml volume) or free DNA (50 μg pRSVL DNA in a 2 ml volume) through a sucrose density gradient. FIG. 2B shows the distribution of the $^3$H and $^{32}$P markers following ultracentrifugation of the DNA-lipid complex (formed via mixing of 20 μmoles DC-Chol/DOPE (2:3) liposomes and 0.4 mg pRSVL DNA in 2 ml volume) through a sucrose density gradient.

Figure 3:
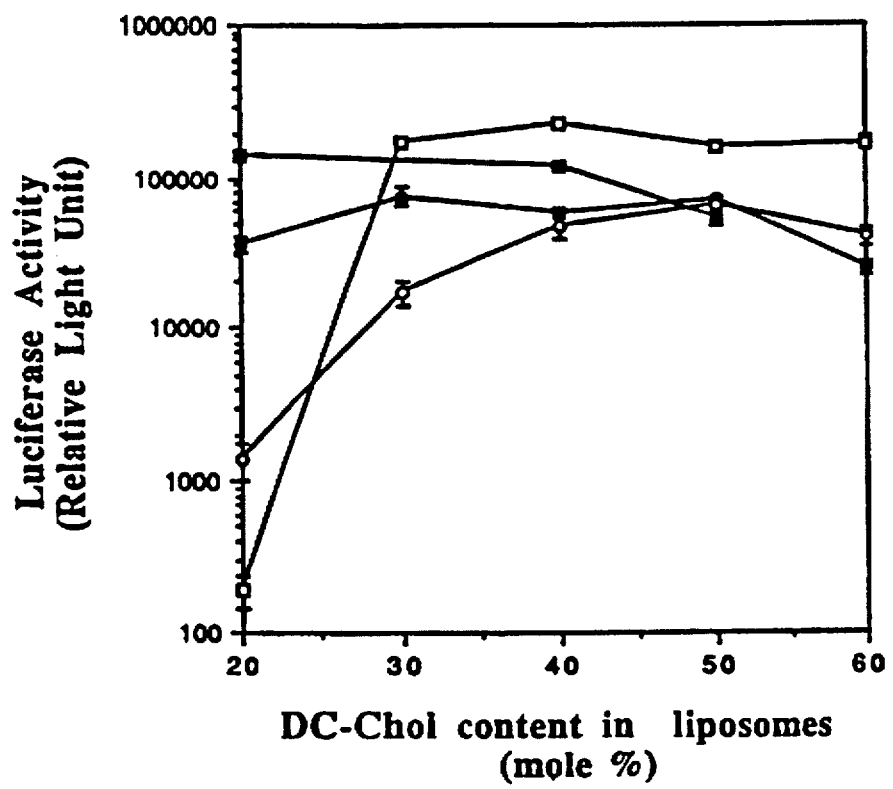

FIG. 3 shows the transfection activities in CHO cells of admixture DNA/liposome complex (○), admixture DNA/liposome/poly-L-lysine(PLL) complex (□) DNA/lipid complex (●) and DNA/lipid/PLL complex (■). The DC-Chol/DOPE liposomes used to form the above complexes contained varying mole% of DC-Chol as indicated at the bottom of FIG. 3. The DNA/lipid (●) and DNA/lipid/PLL (■) complexes were purified on a sucrose density gradient prior to being assayed for transfection activity. Transfection activity is indicated on the vertical axis as relative light units of luciferase activity.

Figure 4:
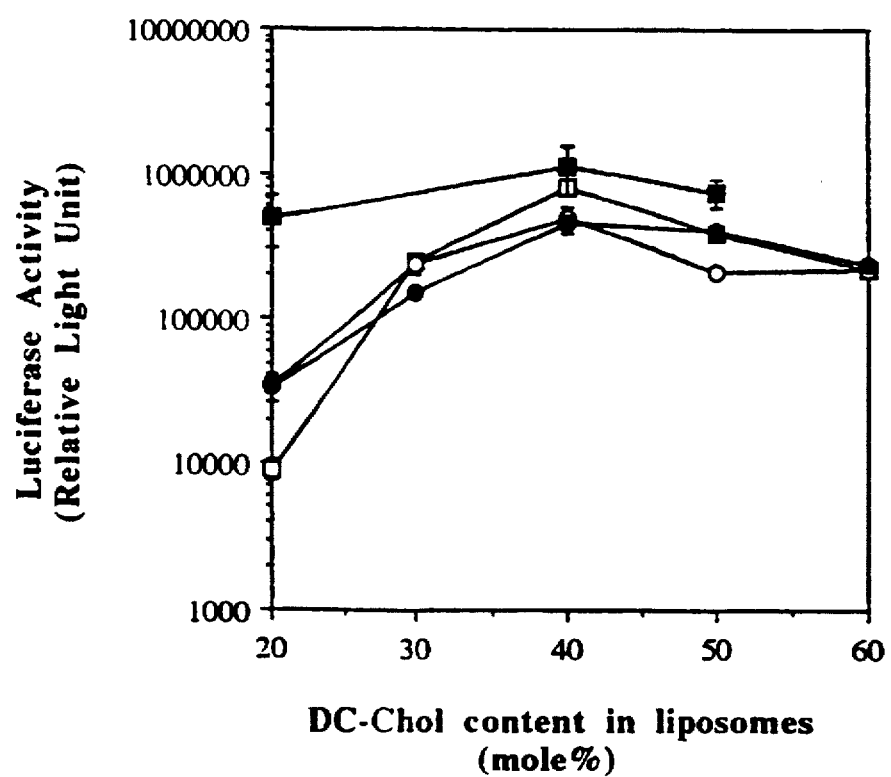

FIG. 4 shows the transfection activities of admixture DNA/liposome complex (○) and admixture DNA/liposome/PLL complex (□) compared to the transfection activities of DNA/lipid (●) and DNA/lipid/PLL complexes stored at 4° C. for 130 days following their purification on a sucrose density gradient. The DC-Chol/DOPE liposomes used to form the above complexes contained varying moles of DC-Chol as indicated at the bottom of FIG. 4. Transfection activity is indicated on the vertical axis as relative light units of luciferase activity.

Figure 5:
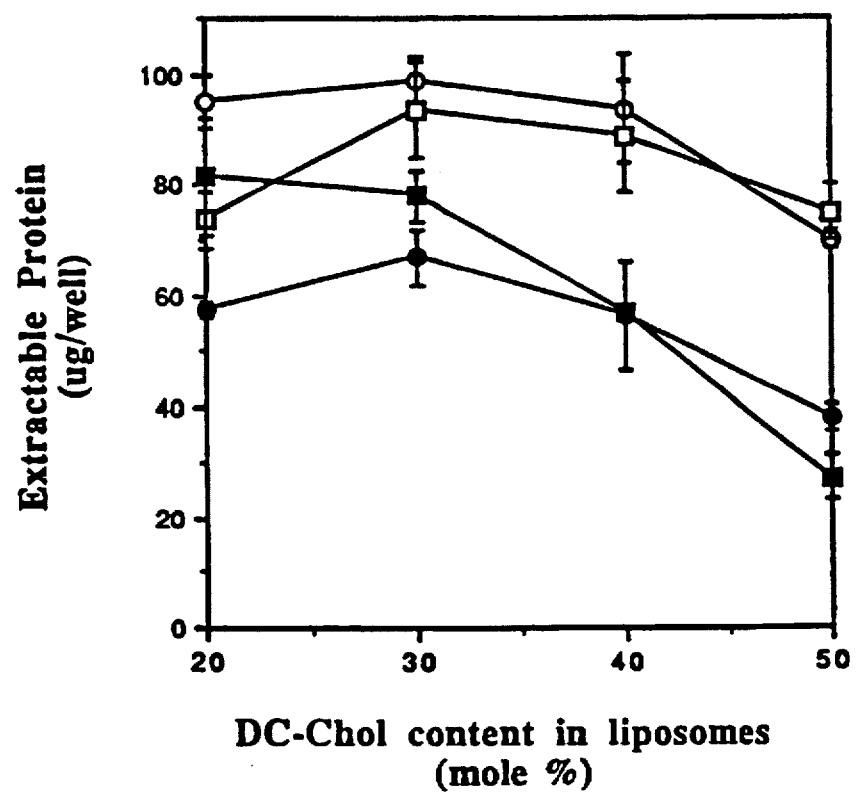

FIG. 5 shows the concentration of extractable protein from CHO cells, 36 hours after the cells were treated with admixture DNA/liposome complex (○); admixture DNA/liposome/PLL complex (□); DNA/lipid complex (●); or DNA/lipid/PLL complex (■). The DNA/lipid and DNA/lipid/PLL complexes were purified on a sucrose density gradient prior to being assayed for transfection activity. The DC-Chol/DOPE liposomes used to form the above complexes contained varying mole% of DC-Chol as indicated at the bottom of FIG. 5.

Figure 6:
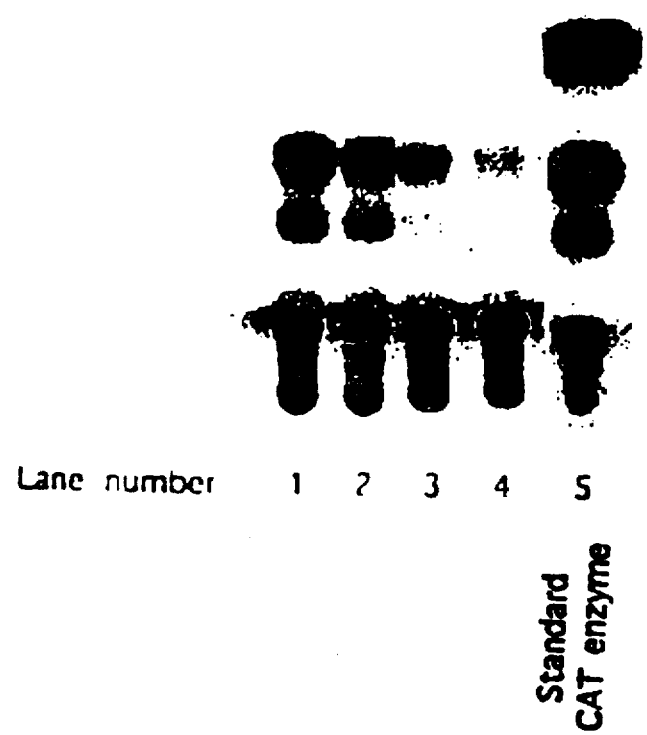

FIG. 6 shows the results of CAT assays of tumor extracts prepared from mice having ovarian tumors. $2 \times 10^6$ human ovarian carcinoma cells were subcutaneously injected into SCID mice at day 0. On day 14, 100 μl solutions containing pUCCMVCAT DNA (contains the chloramphenicol acetyl transferase gene of E. coli) 30 μg) complexed with DC-Chol liposomes (30 nmoles) in the form of admixture (lanes 1 and 2; duplicate samples) or the same amount of DNA in the form of purified complex (prepared from DNA:DC-chol liposome at ratio 1 μg/25 nmoles, lanes 3 and 4; duplicate samples) were directly injected into tumors. 48 hours following transfection, the mice were sacrificed and tumor extract containing 100 μg protein was assayed for CAT activity. Lane 5 shows positive control CAT activity for standard E. coli CAT.

DESCRIPTION OF INVENTION

This invention relates to lipid-comprising drug delivery complexes having a net positive charge at pH 6.0–8.0. These complexes comprise cationic lipids, drugs, and optionally further comprise polycations. The invention further relates to a method for producing these complexes where the method may optionally include the step of purifying these formulations from excess individual components. For the production of the drug/lipid complexes of this invention, inclusion of the purification step is a preferred embodiment. It should be understood that where the purification step is applied to the drug/lipid/polycation complexes, the recovery of these complexes in a pure state free from excess components following purification is lower than the recovery of drug/lipid complexes following their purification since the peak containing the drug/lipid/polycation complex following sucrose purification via density centrifugation is broader than the peak containing drug/lipid complexes and hence, overlaps with the peaks of the free components.

The lipid-comprising drug delivery complexes of this invention are stable, capable of being produced at relatively high concentrations, and retain biological activity of the drug component over time in storage. The method of producing these complexes is based on a binding model between two oppositely charged polymers (e.g. negatively charged nucleic acid and positively charged lipids) in which the formation of large unstable aggregates is avoided by neutralizing the negative charge of the drug via the use of an excess amount of positive charge in the form of cationic liposomes or cationic liposomes and polycation. The complexes of this invention have been observed to retain their initial diameter and bioactivity over 4 months in storage in 10% sucrose buffer.

The "drug" which is contained in the lipid-comprising drug delivery complexes of the present invention may be nucleic acids, polyanionic proteins, polysaccharides and other macromolecules which can be complexed directly with cationic lipids. However, cationic drugs (eg large cationic protein) can be directly complexed with an anionic lipid or sequentially complexed first with anionic lipid or polymer followed by cationic lipid. The use of this process permits delivery of positive or neutral charged drug to cells by the complexes of the present invention.

To produce drug/lipid and drug/lipid/polycation complexes with a net positive charge, the positive charge excess of lipid to drug or of lipid and polycation to drug may be up to about a 30-fold positive charge excess in the complex of total lipids to drug or of lipid and polycation to drug, preferably about a 2 to 10-fold charge excess and most preferably about a 2 to 6-fold charge excess. To produce a nucleic acid/lipid complex having a positive charge excess of lipid to nucleic acid, mole amounts of cationic liposomal lipid to be mixed with 1 µg of nucleic acid to produce a nucleic acid/lipid complex which has positive charge excess of lipid to nucleic acid at pH 6.0–8.0 may range from about 0.1 nmol to about 200 nmol of lipid, preferably about 5 nmol to about 100 nmol lipid, depending on the positive charge content of the cationic liposome. Of course, if the drug were a protein, the amount of lipid to be mixed with 1 µg of negatively charged protein would be at least 10-fold less than the amount of lipid to be mixed with 1 µg of DNA as shown above since proteins are less charge dense than nucleic acids. Those of ordinary skill in the art would readily understand that depending upon the positive charge content of the cationic liposomes, different mole amounts of different cationic liposomes would have to be mixed with an equivalent amount of drug to produce a positive charge excess of lipid to drug.

When a drug/lipid/polycation complex having a net positive charge is to be produced, the inclusion of the polycation reduces the amount of lipid which must be mixed with drug to the extent that the positive charge from the lipid may be less than the negative charge from the drug. This reduction in the amount of lipid reduces the toxicity of the polycation-containing formulations. Mole amounts of cationic liposomes to be used in formulating nucleic acid/lipid/ polycation complexes may range from about 0.1 nmol to about 200 nmol lipid per 1 µg nucleic acid, more preferably from about 1 to about 25 nmoles lipid per 1 µg nucleic acid depending on the positive charge content of the cationic liposomes. It is to be generally understood that in producing the nucleic acid/lipid and nucleic acid/lipid/polycation complexes of the present invention, the mole amount of liposomes required to produce these complexes will increase as the concentration of nucleic acid mixed with the liposomes is increased.

Those of ordinary skill in the art would readily understand that when the complexes of the present invention are purified, the positive charge excess of cationic liposomes to drug or of cationic liposomes and polycation to drug immediately prior to mixing will be greater than the positive charge excess in the purified complexes of lipid to drug or of lipid and polycation since the purification step results in the removal of excess free lipids and/or free polycation.

In order to illustrate how the charges attributed to cationic lipid, drug and polycation may be determined at pH 6.0–8.0 the following example is provided. Assuming the drug to be delivered is DNA, one determines the negative charge of the DNA to be delivered by dividing the amount of DNA to be mixed, or the amount of DNA in the complex, by 330, the molecular weight of a single nucleotide where one nucleotide equals one negative charge. Thus, the negative charge for 1 µg of DNA is 3.3 nmols.

For 10 nmol of DC-Chol/DOPE (2:3) liposomes one calculates the effective charge of the lipid by multiplying the amount of total liposomal lipid (10 nmol) by 0.4 (40% of the total liposomal lipid is the cationic lipid DC-Chol) to yield 4 nmol DC-Chol lipid in the liposomes. Since at pH 6–8, one molecule of DC-Chol has one positive charge, the effective positive charge of liposomal lipid at the time of mixing, or in the complex, is 4.0 nmol. Of course, those of skill in the art would readily understand that other cationic lipids may have a lesser or greater amount of positive charge per molecule of cationic lipid at pH 6–8.0 than DC-Chol.

Assuming the polycation is poly-L-lysine (PLL) the positive charge of PLL is obtained by dividing the amount of PLL to be mixed, or the amount of PLL contained in the complex, by 200, the molecular weight of one lysyl residue where one lysyl residue equals one positive charge. Thus, the positive charge for 1 µg of PLL is 5.0 nmols.

Application of the above calculations to data presented in Table 1 herein (see Example 3) illustrates how a positive to negative charge ratio can be calculated both at the time of mixing of DNA and liposome and, after purification of the complex produced by the mixing of DNA and liposome. In Table 1 of Example 3, 0.4 mg of DNA is mixed with 20 µmols of cationic DC-Chol/DOPE liposomes to produce DNA/lipid complex. For cationic liposomes having a DC-Chol/DOPE ratio of 4:6, the positive charge content of the liposomal lipid is calculated to be 8000 nmol and the negative charge content of the 0.4 mg DNA to be mixed with liposomes is calculated to be 1320 nmols based on the sample calculations presented in the above paragraphs. Therefore, the positive to negative charge ratio at the time of mixing is 6.06 (8000 divided by 1320). However, after the complex was purified, the lipid to DNA ratio of this purified complex was 12.7 nmol lipid/µg DNA as shown in Table 1 (see the "4:6 row"). This 12.7 ratio translates to a positive to negative charge ratio of 1.5 thus showing that purification removed excess positive charge of free liposomes.

Also in Table 1, where DNA/lipid/PLL complex was prepared by mixing 4 µmol of liposomes (4:6 DC-Chol/ DOPE) and 1 mg PLL with 0.4 mg DNA, one can calculate the positive to negative charge ratio at the time of mixing as follows. Based on the sample calculations presented in the above paragraphs, the 4 µmol liposomal lipid contributes 1600 nmol of positive charge, the 1 mg of PLL contributes 5000 nmol of positive charge and the 0.4 mg DNA contributes 1,320 nmol of negative charge. Thus, the positive to negative charge ratio at the time of mixing liposomes, PLL and DNA is $$5 \frac{(1600 + 5000)}{1320}.$$

In a preferred embodiment, the drug is a nucleic acid sequence, preferably a nucleic acid sequence encoding a gene product having therapeutic utility.

In one embodiment of the invention, a method for producing nucleic acid/lipid complexes having a net positive charge at pH 6–8.0, comprises, combining nucleic acids with cationic liposomes in a nucleic acid to lipid ratio such that the nucleic acid/lipid complex formed has a positive charge excess of lipid to nucleic acid.

In an alternative embodiment, nucleic acid and cationic liposome may be mixed with a polycation in a nucleic acid to lipid to polycation ratio such that the nucleic acid/lipid/polycation complexes formed have a positive charge excess of lipid and polycation to nucleic acid at pH 6–8.

In a preferred embodiment, the nucleic acid/lipid and nucleic acid/lipid/polycation complexes are produced by slowly adding nucleic acid to the solution of liposome or liposome plus polycation and mixing with a stirring bar where the mixing is allowed to proceed second. Alternatively, the liposome or liposome/polycation mix can be added into a single chamber from a first inlet at the same time the nucleic acid is added to the chamber through a second inlet. The components are then simultaneously mixed by mechanical means in a common chamber.

The cationic liposomes mixed with drug or with drug and polycation to form the complexes of the present invention may contain a cationic lipid alone or a cationic lipid in combination with a neutral phospholipid. Suitable cationic lipid species include, but are not limited to: 1,2bis (oleoyloxy)-3-(trimethylammonio) propane (DOTAP); N-[1,-(2,3-dioleoyloxy)propyl]-N,N,N-trimethyl ammonium chloride (DOTMA) or other N-(N, N-1-dialkoxy)-alklyl-N,N,N-trisubstituted ammonium surfactants; 1,2 dioleoyl-3-(4'-trimethylammonio) butanoyl-sn-glycerol (DOBT) or cholesteryl (4' trimethylammonia) butanoate (ChOTB) where the trimethylammonium group is connected via a butanoyl spacer arm to either the double chain (for DOTB) or cholesteryl group (for ChOTB); DORI (DL-1,2-dioleoyl-3-dimethylaminopropyl-B-hydroxyethylammonium) or DORIE (DL-1,2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as doctadecylamidoglycylspermine (DOGS) and dipalmitoyl phosphatidyesthanolamidospermine (DPPES) or the cationic lipids disclosed in U.S. Pat. No. 5,283,185, cholesteryl-3β-carboxyl-amido-ethylenetrimethylammonium iodide, 1-dimethylamino-3-trimethylammonio-DL-2-propylcholesteryl carboxylate iodide, cholesteryl-3β-carboxyamidoethyleneamine, cholesteryl-3β-oxysuccinamido-ethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N-(N',N'-dimethylaminoethane)carbamoyl] cholesterol (DC-chol), and 3β-[N-(polyethyleneimine)-carbamoyl]cholesterol.

Examples of preferred cationic lipids include cholesteryl-3β-carboxyamidoethylenetri-methylammonium iodide, 1-dimethylamino-3-trimethylammonio-DL-2-propylcholesteryl carboxylate iodide, cholesteryl-3β-carboxyamidoethyleneamine, cholesteryl-3β-oxysuccin-amidoethylenetrimethylammonium iodide, 1-dimethylamino-3-trimethylammonio-DL-2-propyl-cholesteryl-3β-oxysuccinate iodide, 2-[(2-trimethylammonio)ethylmethylamino|ethyl-cholesteryl-3β-oxysuccinateiodide, 3β[N-(N',N'dimethyl-aminoethane)-carbamoyl]-cholesterol (DC-chol), and 3β[N-(polyethyleneimine)-carbamoyl]cholesterol.

Since an attribute of the complexes of the invention is their stability during storage (i.e., their ability to maintain a small diameter and retain biological activity over time following their formation); it will be understood by those of ordinary skill in the art that preferred cationic lipids are those lipids in which bonds between the lipophilic group and the amino group are stable in aqueous solution. While such bonds found in cationic lipids include amide bonds, ester bonds, ether bonds and carbamoyl bonds, preferred cationic lipids are those having a carbamoyl bond. An example of a preferred cationic lipid having a carbamoyl bond is DC-Chol. Those of skill in the art would readily understand that liposomes containing more than one cationic lipid species may be used to produce the complexes of the present invention. For example, liposomes comprising two cationic lipid species, lysyl-phosphatidylethanolamine and β-alanyl cholesterol ester have been disclosed (Brunette, E. et al. (1992) *Nucl. Acids Res.*, 20:1151).

It is to be further understood that in considering cationic liposomes suitable for use in mixing with drug and optionally with polycation, to form the complexes of this invention, the methods of the invention are not restricted only to the use of the lipids recited above but rather, any lipid composition may be used so long as a cationic liposome is produced.

Thus, in addition to cationic lipids, cationic liposomes used to form the complexes of the invention may contain other lipids in addition to the cationic lipids. These lipids include, but are not limited to, lyso lipids of which lyso-phosphatidylcholine (1-oleoyllysophosphatidycholine) is an example, cholesterol, or neutral phospholipids including dioleoyl phosphatidyl ethanolamine (DOPE) or dioleoyl phosphatidylcholine (DOPC). The lipid complexes of the invention may also contain negatively charged lipids as well as cationic lipids so long as the net charge of the complexes formed is positive. Negatively charged lipids of the invention are those comprising at least one lipid species having a net negative charge at or near physiological pH or combinations of these. Suitable negatively charged lipid species comprise phosphatidyl glycerol and phosphatidic acid or a similar phospholipid analog.

It is further contemplated that in the cationic liposomes utilized to form the complexes of the invention, the ratio of lipids may be varied to include a majority of cationic lipids in combination with cholesterol or with mixtures of lyso or neutral lipids. When the cationic lipid of choice is to be combined with another lipid, a preferred lipid is a neutral phospholipid, most preferably DOPE.

Methods for producing the liposomes to be used as in the product of the lipid-comprising drug delivery complexes of starting components the present invention are known to those of ordinary skill in the art. A review of methodologies of liposome preparation may be found in *Liposome Technology* (CFC Press NY 1984); *Liposomes* by Ortro (Marcel Schher, 1987); *Methods Biochem Anol.* 33:337–462 (1988) and U.S. Pat. No. 5,283,185. Such methods include freeze-thaw extrusion and sonication. Both unilamellar liposomes (less than about 200 nm in average diameter) and multilamellar liposomes (greater than about 300 nm in average diameter) may be used as starting components to produce the complexes of this invention.

In the cationic liposomes utilized to produce the drug/lipid complexes of this invention, the cationic lipid is present in the liposome at from about 10 to about 100 mole % of total liposomal lipid, preferably from about 20 to about 80 mole % and most preferably about 20 to about 60 mole %. The neutral lipid, when included in the liposome, may be present at a concentration of from about 0 to about 90 mole % of the total liposomal lipid, preferably from about 20 to about 80 mole %, and most preferably from 40 to 80 mole %. The negatively charged lipid, when included in the liposome, may be present at a concentration ranging from about 0 mole % to about 49 mole % of the total liposomal lipid, preferably from about 0 mole % to about 40 mole %. In a preferred embodiment, the liposomes contain a cationic and a neutral lipid, most preferably DC-Chol and DOPE in ratios between about 2:8 to about 6:4. It is further understood that the complexes of the present invention may contain modified lipids, protein, polycations or receptor ligands which function as a targeting factor directing the complex to a particular tissue or cell type. Examples of targeting factors include, but are not limited to, asialoglycoprotein, insulin, low density lipoprotein (LDL), folate and monoclonal and polyclonal antibodies directed against cell surface molecules. Potential targets include, but are not limited to, liver, blood cells, endothelial cells and tumor cells.

It is to be further understood that the positive charge of the complexes of this invention may be affected not only by the lipid composition of the complex but also by the pH of the solution in which the drug/lipid complexes are formed. For example, increasing pH (more basic) will gradually neutralize the positive charge of the tertiary amine of the cationic lipid DC-Chol. In a preferred embodiment, the complexes of the present invention are produced, and stored, at a pH such that the complexes have a net positive charge. A preferred pH range is pH 6.0–8.0, most preferably pH 7.0–7.8.

When a polycation is to be mixed with nucleic acid and cationic liposomes, the polycation may be selected from organic polycations having a molecular weight of between about 300 and about 200,000. These polycations also preferably have a valence of between about 3 and about 1000 at pH 7.0. The polycations may be natural or synthetic amino acids, peptides, proteins, polyamines, carbohydrates and any synthetic cationic polymers. Nonlimiting examples of polycations include polyarginine, polyornithine, protamines and polylysine, polybrene (hexadimethrine bromide), histone, cationic dendrimer, spermine, spermidine and synthetic polypeptides derived from SV40 large T antigen which has excess positive charges and represents a nuclear localization signal. A preferred polycation is poly-L-lysine (PLL). In producing nucleic acid/lipid/polycation complexes of the present invention, the ratio of polycation to nucleic acid is kept fixed while varying the amount of liposome. However, those of skill in the art would recognize that the ratio of polycation to nucleic acid will be affected by the charge density of the liposome to be mixed with the nucleic acid and polycation. For example, if the charge density of liposomes is decreased as a result of changes in the lipid composition of the liposome (eg decreasing the ratio of cationic lipid: neutral lipid in the liposome), the amount of polycation to be mixed with nucleic acid and liposome may be increased to compensate for the decrease in positive charge contributed by the liposomes. However, when polycation is utilized, it is preferred to use subsaturating amounts of polycation (ie amounts which will not saturate all the negative charge of the nucleic acid) in order to allow the cationic lipids to complex with the nucleic acid. Thus, in a preferred embodiment of the invention, a positive charge excess of lipid to nucleic acid is used even when polycation is mixed with lipid and nucleic acid. Amounts of polycation which may be mixed with 1 µg of nucleic acid and varying amounts of cationic liposomes in the present invention range from about 0.01 µg to about 100 µg of polycation per µg of nucleic acid, preferably from about 0.1 µg to about 10 µg of polycation per µg of nucleic acid.

Where purification of nucleic acid/lipid and nucleic acid/lipid/polycation complexes from excess free DNA, free liposomes and free polycation is desired, purification may be accomplished by centrifugation through a sucrose density gradient or other media which is suitable to form a density gradient. However, it is understood that other methods of purification such as chromatography, filtration, phase partition, precipitation or absorption may also be utilized. In a preferred method, purification via centrifugation through a sucrose density gradient is utilized. The sucrose gradient may range from about 0% sucrose to about 60% sucrose, preferably from about 5% sucrose to about 30% sucrose. The buffer in which the sucrose gradient is made can be any aqueous buffer suitable for storage of the fraction containing the complexes and preferably, a buffer suitable for administration of the complex to cells and tissues. A preferred buffer is pH 7.0–8.0 Hepes.

It is understood that in the present invention, preferred nucleic acid sequences are those capable of directing protein expression. Such sequences may be inserted by routine methodology into plasmid expression vectors known to those of skill in the art prior to mixing with cationic liposomes or liposomes and polycation to form the lipid-comprising drug delivery complexes of the present invention. The amount of nucleic acid mixed together with cationic liposomes or with cationic liposomes and polycation may range from about 0.01 µg to about 10 mg, preferably from about 0.1 µg to about 1.0 mg. It is understood that where the nucleic acid of interest is contained in plasmid expression vectors, the amount of nucleic acid recited above refers to the plasmid containing the nucleic acid of interest.

The purification of the nucleic acid/lipid and nucleic acid/lipid/polycation complexes of the present invention serves to concentrate the nucleic acids and lipids contained in the resultant complexes from about 50-fold to about 500-fold such that the lipid content contained in the complexes may be as high as about 40 µmol/ml and the nucleic acid content may be as high as about 2 mg/ml.

The diameter of the complexes produced by the methods of the present invention is less than about 400 nm, preferably less than about 200 nm, and more preferably less than 150 nm.

The complexes formed by the methods of the present invention are stable for up to about one year when stored at 4° C. The complexes may be stored in 10% sucrose solution upon collection from the sucrose gradient or they may be lyophilized and then reconstituted in 10% sucrose solution prior to use. In a preferred embodiment, the complexes are stored in solution. The stability of the complexes of the present invention is measured by specific assays to determine the physical stability and biological activity of the complexes over time in storage. The physical stability of the complexes is measured by determining the diameter of the complexes by methods known to those of ordinary skill in the art, including for example, electron microscopy, gel filtration chromatography or by means of quasi-elastic light scattering using a Coulter N4SD particle sizes as described in the Examples. The physical stability of the complex is "substantially unchanged" over storage when the diameter of the stored complexes is not increased by more than 100%, preferably by not more than 50%, and most preferably by not more than 30%, over the diameter of the complexes as determined at the time the complexes were purified.

Assays utilized in determining the biological activity of the complexes vary depending on what drug is contained in the complexes. For example, if the drug is nucleic acid encoding a gene product, the biological activity can be determined by treating cells in vitro under transfection conditions utilized by those of ordinary skill in the art for the transfection of cells with admixtures of DNA and cationic liposomes. Cells which may be transfected by the complexes includes those cells which may be transfected by admixture DNA/liposome complexes. The activity of the stored complexes is then compared to the transfection activity of complexes prepared by admixture. If the drug is a protein, then activity may be determined by a bioassay suitable for that protein.

It is further understood by those of skill in the art that the complexes of the present invention may be used in vivo as vectors in gene therapy. Therapeutic formulations using the complexes of the invention preferably comprise the complexes in a physiologically compatible buffer such as, for example, phosphate buffered saline, isotonic saline or low ionic strength buffer such as 10% sucrose in $H_2O$ (pH 7.4–7.6) or in Hepes (pH 7–8, a more preferred pH being 7.4–7.6). The complexes may be administered as aerosols or as liquid solutions for intratumor, intravenous, intratracheal, intraperitoneal, and intramuscular administration.

Any articles or patent referenced herein are incorporated by reference. The following examples illustrate various aspects of the invention but are intended in no way to limit the scope thereof.

EXAMPLES

Materials

DOPE was purchased from Avanti Polar Lipid, Inc. (Alabaster, Ala.). PRSVL, a plasmid which encodes the luciferase gene under the control of Rous sarcoma virus long terminal repeat, (De Wet, J. R. et al. (1987) Mol. Cell. Biol., 7: 725–737) was amplified in E. coli and purified using the standard CsCl-EtBr ultracentrifugation method (Sambrook, J., Fritsch, E. F. and Maniatis, T., Molecular Cloning: A Laboratory Manual (2d ed) Cold Spring Harbor Laboratory Press: New York (1989)). All the tissue culture media were obtained from Gibco BRL (Gaithersburg, Md.). CHO (Chinese Hamster Ovary cells) and BHK (Baby Hamster Kidney cells) cells were from American Type Culture Collection (Rockville, Md.). Mouse lung cells (MLC) are primary culture cells originally derived from the lung of a Balb/c mouse by Dr. S. Kenned (Oak Ridge National Laboratory, Tenn.). BHK and MLC cells were cultured with DMEM media, and CHO cells were cultured with F12 media. All media was supplemented with 10% fetal bovine serum (Hyclone Laboratories, Inc., Logan, Utah) and 100 unit/ml penicillin and 100 µg/ml streptomycin. Poly-L-lysine (MW 3000 and MW 25,600) and other chemicals were from Sigma (St Louis, Mich.).

DC-Chol was synthesized according to the method of Gao and Huang (1991) (Gao, X., and Huang, L. (1991) Biochem. Biophys. Res. Commun., 179: 280–285) with modifications in the purification steps as follows: after the reaction, 10 ml hexane was added and the mixture was extracted three times with 10 ml water. The organic phase was collected and dried under vacuum at 4° C. The resulting solid was dissolved in a minimal amount of absolute ethanol with heat, and recrystallized in acetonitrile at 0° C. The purity of DC-Chol was at least >95%, as analyzed by TLC method and $^1$H-NMR and the yield of about 70% was a significant improvement over that of the previously reported method of Gao, X., and Huang, L. ((1991) Biochem. Biophys. Res. Commun., 179: 280–285).

Methods

Preparation and purification of complexes

Cationic liposomes at a 20 mM total lipid concentration were prepared from DC-Chol and DOPE at various ratios by a sonication method, according to a published procedure (Gao, X., and Huang, L. (1991) Biochem. Biophys. Res. Commun., 179: 280–285). Trace amount of [$^3$H] cholesteryl hexadecyl ether (Amersham, Arlington Heights, Ill.) was included for quantitation purpose. The size of these liposomes was between 100 to 150 nm in diameter, as determined by quasi-elastic light scattering using a Coulter N4SD particle sizer (Coulter Electronics, Inc., Hialeah, Fla.). Unless indicated otherwise in the following Examples, DNA/lipid complexes were prepared at a typical laboratory scale by adding amounts of free DC-Chol/DOPE liposomes as indicated in each Example in a volume of 1 ml of a 2 mM Hepes buffer (pH 7.6) to a 15×7.5 polystyrene culture tube (Baxter, McGraw Pare, Ill.), a micro-magnetic stirrer was placed in the tube, and the solution was well mixed. Amounts of pRSVL DNA as indicated in each Example were then added dropwise from a stock solution (0.2 mg/ml, in 2 mM Hepes buffer, pH 7.6) to the liposome solution over a period of 3 min. Trace amounts of pRSVL labeled with 32P using a nick translation kit (Promega, Madison, Wis.) and [32P] dCTP (Amersham, Arlington Heights, Ill.) was included for the purpose of quantitation. To prepare lipid/PLL/DNA complexes, an amount of the above 0.2 mg/ml DNA solution as indicated in each Example was added to 1 ml PLL/liposome mixture containing amounts of liposomes and PLL as indicated in each Example. DNA/lipid complexes were loaded on the top of a sucrose step gradient composed of 0.5 ml each of 5%, 7.5%, 10% and 15% sucrose (w/w) and DNA/lipid/PLL complexes were loaded on top of a sucrose step gradient composed of 0.5 ml each of 5%, 10%, 15%, 20%, 25% and 30% sucrose (w/w). The DNA/lipid and DNA/lipid/PLL complexes were then purified from free lipid and PLL by ultracentrifugation at 100,000 g for 30 min at 4° C. After centrifugation, fractions of 200 µl were taken from the top to the bottom of the tube. Aliquots from each fraction were assayed for both $^3$H and $^{32}$P radioactivity using a scintillation counter. Fractions that contained peak value of the 32P were collected and pooled. These pooled fractions were then assayed for particle size and for transfection activity.

In vitro Transfection assay

The biological activity of the above complexes were assayed by in vitro transfection on three types of cells. Briefly, cells grown in 48 well plate were incubated with DNA/lipid complex diluted in 0.5 ml CHO-S-SFM (Gibco BRL) or with admixture DNA/liposome complex prepared according to Gao and Huang (1991) (Gao, X., and Huang, L. (1991) Biochem. Biophys. Res. Commun., 179: 280–285). For transfection of PRSVL DNA using DC-Chol liposomes in the presence of PLL, liposomes were first mixed with PLL, then complexed with DNA. All transfections were performed for 4 hours at 37° C. After transfection, cells were further cultured for 36 hours in the appropriate media containing 10% fetal bovine serum. Cells were then washed with PBS and lysed with 100 µl of 1X lysis buffer provided by a luciferase assay kit (Promega, Madison, Wis.). A 4 µl sample of the lysate was assayed for luciferase activity using 100 µl substrate solution from the reconstituted luciferase assay kit and an AutoLumat LB953 luminometer (Berthold, Germany). Protein concentration from each lysate was assayed by a Coomassie blue dye method according to the manufacturer's protocol (Pierce, Rockford, Ill.).

EXAMPLE 1

The Size of the DNA/Lipid Complex is Determined by the Ratio of DNA to Lipid This experiment was conducted to show that the size of the DNA-lipid complex formed by admixture changed as the ratio of DNA mixed with liposome varied. In brief, pRSVL plasmid DNA (2 µg) was mixed with varying amounts of DC-CHOL/DOPE (3:2) liposomes in 2 mM Hepes buffer at pH 7.6 in a final volume of 500 AL and after 7 minutes, the size of the complex was determined with a Coulter N4SD laser light scattering particle sizer operating in the unimodel mode.

Figure 1:
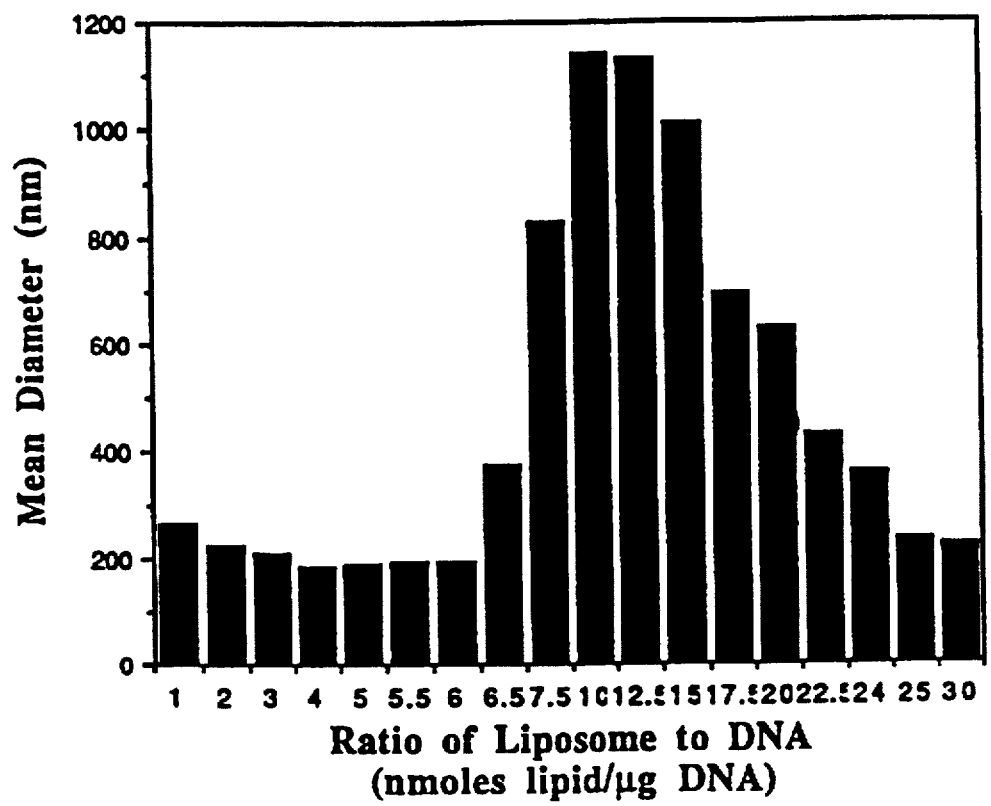
FIG. 1 shows a typical size distribution (mean diameter) of nucleic acid/liposome complexes prepared as an admixture from DC-Chol/DOPE (3:2) liposomes and PRSVL plasmid DNA (2 μg) at the indicated lipid to DNA ratios.

As shown in FIG. 1, large aggregates did not form when DNA was in excess (ratios of liposome to DNA less than 7) but at ratios of lipid to DNA that were charge neutral (~10), the size of the complex reached a maximum. In addition, when the ratio of liposome-to-DNA was kept constant at 10 nmoles/µg, the size of the complex increased as both DNA and liposome concentration increased and eventually formed precipitates. However, when the ratio of liposomes to DNA was increased, the size of the complex was progressively reduced until the size of the complex became constant (250–300 nm) when the ratio of liposome-to-DNA exceeded 25 nmoles lipid/µg DNA. This result may be due to the fact that the DNA was perhaps coated by excess liposomes and therefore aggregation between the complexes did not occur.

Based on the data presented in FIG. 1, lipid/DNA complexes were prepared using a liposome-to-DNA ratio of 50 nmoles/µg by slowly adding a DNA solution of 200 µg/ml to an excess amount (10 µmols) of liposome. The size of the complex formed was about 250 nm. When the ratio of liposome-to-DNA was changed to 25 nmoles/µg, the size of the complex increased to about 350 nm. The complexes formed using either the 25 nmole/µg or 50 nmole/µg ratios appeared to be physically stable since no precipitates formed during storage for four weeks at 4° C.

EXAMPLE 2

Purification of DNA/lipid Complexes

When DNA was mixed with liposomes at a ratio of 1 µg/50 nmoles, an excess of free liposomal lipids was observed to co-exist with the DNA/lipid complex. Since excess free lipids are toxic to cells, an experiment was conducted to determine if free liposomal lipids could be separated from the DNA/lipid complex by a density gradient ultracentrifugation method. In brief, free liposomes (10 µmoles of DC-Chol/DOPE (2:3) in a volume of 2 ml); free DNA (50 µg pRSVL in a volume of 2 ml) and DNA/lipid complex formed by mixing 20 µmoles DC-Chol/DOPE (2:3) and 0.4 mg pRSVL plasmid DNA (50 nmoles/µg) were each centrifuged for 30 minutes at 4° C. at 100,000 g over a gradient consisting of 0.5 ml each of 5%, 7.5%, 10% and 15% sucrose (W/W). Fractions of 200 µl were then collected from the top to the bottom of the tube and assayed for the distribution of DNA marker ($^{32}$P, ■) and lipid marker ($^{3}$H, ○). FIGS. 2A and 2B show the results of typical separations of free liposomal lipid, free DNA (FIG. 2A) and DNA/lipid complex (FIG. 2B) on the sucrose gradient. The results presented in FIG. 2B show that after centrifugation, the complex formed a major band at the 10% sucrose layer. By comparison, FIG. 2A shows that most of the radioactivity of the free DNA or free liposomal lipids distributed at the top half of the tube and did not enter the sucrose gradient. In addition, although the peak of $^{3}$H and the peak of $^{32}$P in FIG. 2B co-existed at fraction number 16, there was a significant amount of the $^{3}$H distributed in fractions 1 to 10 indicating that the excess free liposomal lipids were well separated from the DNA/lipid complex.

EXAMPLE 3

Physical Stability of Purified Lipid/DNA and Lipid/PLL/DNA Complexes

DNA/lipid complexes were formed by mixing 20 µmoles of liposomes of various DC-Chol/DOPE compositions (see Table 1) with 0.4 mg pRSVL plasmid DNA at a ratio of 1 µg DNA/50 nmoles lipid. Lipid/PLL/DNA complexes were formed by mixing 4 µmoles of liposomes of various DC-Chol/DOPE compositions with 1 mg PLL (MW=3000) and 0.4 mg pRSVL plasmid DNA. Both complexes were then purified from free lipids, free DNA and free PLL by sucrose gradient centrifugation as described in the Methods section. The peak fractions were collected and pooled. Pooled samples were then assayed for diameter immediately after collection (0 days) or after storage in 10% sucrose at 4° C. for 120 days. Table 1 shows the results of these assays.

TABLE 1

Physical stability of purified lipid/DNA and lipid/PLL/DNA pre-complexes

| Liposome composition (DC-chol/DOPE) | PLL (µg/µgDNA) | Size (nm) Day 0 | Size (nm) Day 120 | Purified complex Ratio of lipid/DNA (nmoles/µg) | Recovery of DNA (% Total) |
|---|---|---|---|---|---|
| 2:8 | 0 | 168 | 280 | 23.2 | 51 |
| 3:7 | 0 | 187 | 252 | 14.0 | 66 |
| 4:6 | 0 | 175 | 195 | 12.7 | 73 |
| 5:5 | 0 | 174 | 210 | 13.2 | 70 |
| 6:4 | 0 | 198 | 232 | 10.1 | 69 |
| 2:8 | 2.5 | 165 | 287 | 20.8 | 17 |
| 3:7 | 2.5 | 99 | 101 | 19.2 | 22 |
| 4:6 | 2.5 | 138 | 132 | 38.3 | 29 |
| 5:5 | 2.5 | 184 | 178 | 22.4 | 27 |

The data presented in Table 1 shows that purified lipid/DNA and lipid/PLL/DNA complexes were small (under 200 nm) in size at day 0 and that their size did not increase dramatically with storage. Further, the ratios of DNA-to-lipid in the purified complexes was between 10 to 23 nmoles lipid/μg DNA depending on the composition of the liposomes used and this ratio did not change after storage for 120 days. A reciprocal relationship between the concentration of DC-Chol in the liposomes and the amount of the lipid in the complex was also observed indicating that liposomes enriched with DC-Chol show stronger DNA binding or charge neutralizing activity than liposomes less enriched with DC-Chol. The far-right hand columns shows recovery of $^{32}$P-labeled DNA in the DNA/lipid and DNA/lipid/PLL complexes following their purification on the sucrose density gradient. The results show that recovery of DNA in the non-PLL containing complexes was higher than that observed for the PLL-containing complexes.

EXAMPLE 4

Biological Activity of the Purified Complexes in Various Cells

Since the DNA/lipid complexes formed by a mixture of liposomes to DNA having a high lipid to DNA ratio were both small and stable over time, experiments were conducted to compare the transfection activity of these complexes to the activity of DNA/liposome complex prepared by the admixture method.

In one experiment, CHO cells cultured in 48 well-plates were treated for 4 hours with an admixture of either 1 μg pRSVL and 10 nmoles DC-Chol/DOPE liposomes of different lipid compositions alone (○) or together with 1 μg PLL (MW=3,000) (□) or, the cells were treated with purified DNA/lipid complex (●) or purified DNA/lipid/PLL complex (■) formed by mixing 1 μg DNA with 50 nmoles DC-Chol/DOPE liposomes (DNA/lipid complex) or with 10 nmoles DC-Chol/DOPE liposomes and 1 μg PLL (DNA/lipid/PLL complex) followed by centrifugation through a sucrose density gradient as described in the Methods section. 36 hours after treatment, cells were lysed in 100 μl lysis buffer and 4 μl of the lysate was assayed for luciferase activity using 100 μl of luciferase substrate solution. Luciferase activity was then counted over a period of 20 seconds. The results presented in FIG. 3 show that the most preferred liposome composition for transfecting CHO cells was 40% DC-Chol and 60% DOPE. In addition, in the presence of additional 1 μg poly-L-lysine (PLL, MW=3, 000), a 2–7 fold enhancement of the transfection activity was seen in most cases. Of particular interest, the activity of the purified DNA/lipid complex was similar to that of the admixture DNA/lipid complex when the same amount of DNA was added to cells. However, the transfection activity of the purified DNA/lipid/PLL complex was about 30% to 50% lower than that of the DNA/liposome/PLL complex prepared by the admixture procedure.

In order to determine that the results obtained in CHO cells were not cell-specific, the transfection activities of the purified DNA/lipid and DNA/lipid/PLL complexes in two other cells, BHK and mouse lung cells (MLC), were compared to that of DNA/liposome complexes formed by admixture.

In brief, cells (either BHK or MLC) grown in 48-well plates at 60% confluency were transfected with 1 μg PRSVL complexed with 10 nmoles of DC-Chol liposomes (admixture complex), with the same amount of DNA mixed with liposomes at a DNA/liposome ratio of 1 μg/50 nmols to produce purified DNA/lipid complex or with purified DNA/lipid/PLL complex prepared at a DNA/liposome/PLL ratio of 1 μg/10 nmols/2 μg. Cells were then harvested at 36 hours post-transfection, and the luciferase activity of the transfected cell lysates was determined as described in the Methods section. The results of these experiments are shown in Tables 2 and 3.

TABLE 2

Expression of luciferase gene in BHK cells transfected with pRSVL

| Liposome composition (DC-Chol/DOPE) | Luciferase Activity (Relative Light Units × $10^{-3}$) | | |
|---|---|---|---|
| | Admixture DNA/liposome complex | Purified DNA/lipid complex | Purified DNA/lipid/PLL complex |
| 2:8 | 91.8 ± 9.5 | 110.1 ± 5.2 | 214.6 ± 41.1 |
| 3:7 | 61.2 ± 19.9 | 1886.8 ± 266.7 | 151.7 ± 62.9 |
| 4:6 | 438.2 ± 14.4 | 1638.8 ± 63.9 | 446.3 ± 16.9 |
| 5:5 | 837.8 ± 8 | 1015.0 ± 41.2 | 234.2 ± 46.4 |

TABLE 3

Expression of luciferase gene in mouse lung cells transfected with pRSVL

| Liposome composition (DC-Chol/DOPE) | Luciferase Activity (Relative Light Units × $10^{-3}$) | | |
|---|---|---|---|
| | Admixture DNA/liposome complex | Purified DNA/lipid complex | Purified DNA/lipid/PLL complex |
| 2:8 | 1.1 ± 0.7 | 0.4 ± 0.2 | 0.3 ± 0.1 |
| 3:7 | 1.5 ± 1.0 | 0.3 ± 0.0 | 4.1 ± 1.3 |
| 4:6 | 3.1 ± 0.2 | 2.0 ± 0.3 | 14.6 ± 3.1 |
| 5:5 | 0.1 ± 0.0 | 1.5 ± 1.2 | 10.1 ± 2.3 |

Interestingly, for the BHK cell line, the transfection activity of the purified DNA/lipid complex was significantly higher than that of the DNA/liposome complex formed by admixture. For cells such as MLC, which are difficult to transfect, purified complexes made from DNA/liposome/PLL mixtures were apparently superior to admixture complexes and to purified DNA/lipid complexes made without PLL.

In order to determine whether lipid/PLL/DNA complexes could be made using different ratios of lipid and nucleic acid and a different molecular weight PLL than that used in the previous examples, the following experiment was conducted. Lipid/poly-L-lysine/DNA complex was prepared from 20 μg pRSVL plasmid DNA, 10 μg poly-L-lysine (MW 25,600), and DC-chol/DOPE liposomes (4.5/5.5 molar ratio) at the ratios of lipid to DNA shown in Table 4. The resulting complexes were then purified by sucrose gradient ultracentrifugation as described in the methods section. An aliquot of the purified complex containing 0.5 μg of DNA was used to transfect CHO cells, and luciferase activity was then measured. The results of this experiment are shown below in Table 4.

TABLE 4

Effect of lipid/DNA ratio on purified complex containing poly-L-lysine (MW 25,600)

| Ratio (nmoles lipid/μg DNA) | Composition of purified complex (nmoles lipid/μg DNA) | Size of purified complex (nm) | Transfection activity[b] (counts (SD) × $10^{-3}$) |
|---|---|---|---|
| 3.3  | 1.1 | 89  | 108 (5) |
| 6.6  | 2.5 | 98  | 6,065 (604) |
| 12.5 | 4.3 | 101 | 5,846 (668) |
| 20.0 | 9.6 | 35  | 7,633 (977) |

The results show that in the presence of increased amounts of polycation, lower ratios of lipid to DNA may be used to produce DNA/lipid/polycation complexes having appreciable transfection activity.

EXAMPLE 5

Transfection Activity of Stored Complexes

CHO cells cultured in 48 well-plates were treated for 4 hours with admixture of 1 μg pRSVL and 10 nmoles of DC-Chol/DOPE liposomes of different DC-Chol/DOPE compositions alone (○) or together with 1 μg PLL (mw=3,000) (□), or with purified DNA/lipid (●) or DNA/lipid/PLL (■) complexes stored at 4° C. for 130 days in 10% sucrose. The purified complexes had been formed by mixing 1 μg pRSVL and 50 nmoles of DC-Chol/DOPE liposomes of different DC-Chol/DOPE compositions alone (DNA/lipid) or with 10 nmole of DC-Chol/DOPE liposomes and 1 μg PLL (DNA/lipid/PLL complex) followed by centrifugation through a sucrose density gradient as described in the Methods section. The results show that the luciferase activity of cell lysates prepared from cells transfected with the stored DNA/lipid and DNA/lipid/PLL complexes was comparable with the luciferase activity observed in cell lysates of cells transfected with the corresponding complexes prepared by admixture.

EXAMPLE 6

Comparative Cytotoxicity of DNA/liposome Complexes Prepared by Admixture to that of Purified DNA/Lipid Complexes Cell toxicity of the different complexes was studied in CHO cells as follows. CHO cells were treated with admixture DNA/liposome complex (○), admixture/liposome/PLL complex (□); purified DNA/lipid complex (●); or purified DNA/lipid/PLL complex (■). The admixture complexes were formed by mixing 1 μg pRSVL DNA with 10 nmoles DC-Chol/DOPE liposomes of different DC-Chol/DOPE compositions alone or together with 1 μg PLL (mw=3,000). The purified complexes were formed by mixing 1 μg pRSVL DNA with 50 nmoles DC-Chol/DOPE liposomes alone (DNA/lipid complex) or with 10 nmoles DC-Chol/DOPE liposomes and 1 μg PLL (DNA/lipid/PLL complex) followed by centrifugation through a sucrose density gradient as described in the Methods section. 36 hours after treatment, the cells were lysed, protein was extracted and then quantitated by a Coomassie blue dye method.

FIG. 5 shows the results of this experiment where the amount of total extractable protein recovered at the end of the experiment serves as an indicator of the portion of the cells which survived after the indicated treatment. The data presented shows that while the purified complex appeared to be slightly more toxic to the cells than the admixture DNA/liposome complex, morphologically, the transfection did not cause any serious cytotoxic effects in cells treated with either admixture complexes or the purified complexes, except that the cells treated with purified complexes containing high mole % DC-Chol were less confluent at the end of the experiment.

EXAMPLE 7

In Vivo Transfection of Tumors by Purified DNA/Lipid Complexes $3 \times 10^6$ human ovarian carcinoma cells were injected subcutaneously into SCID mice at day 0. 14 days later, 100 μl solutions containing pUCCMVCAT DNA (30 μg) complexed with DC-Chol (3:2 DC-Chol:DOPE) liposomes (30 nmoles) in the form of admixture (lanes 1 and 2) or the same amount of DNA in the form of purified DNA/lipid complex (prepared from DNA and DC-Chol liposomes at ratios of 1 μg DNA/25 nmoles lipid were directly injected into tumors. Animals were sacrificed 2 days later and tumor extracts containing 100 μg protein were assayed for CAT activity at 37° C. according to Ausubel, et al. (1991) Current Protocols in Molecular Biology (Wiley, Boston), Vol. 1, pp. 9.6.2–9.6.5). The results show that purified complex, while prepared under non-optimal conditions, exhibited in vivo transfection activity.

We claim:

1. A method for producing noncovalent nucleic acid/lipid/polycation complexes having a net positive charge at about pH 6.0–8.0, said method comprising mixing said nucleic acid with cationic liposomes and polycation in a ratio of nucleic acid to lipid to polycation which results in the production of said complexes, said polycation being selected from the group consisting of polyarginine, polyornithine, protamines, polylysine, polybrene (hexadimethrine bromide), histone, cationic dendrimer, spermine, spermidine and synthetic polypeptides derived from SV40 large T antigen, and which synthetic polypeptides have excess positive charges and represent a nuclear localization signal.

2. The method of claim 1, wherein the ratio of lipid to nucleic acid ranges from about 0.1 nmol to 200 nmol lipid per 1 μg nucleic acid.

3. The method of claim 2, wherein the ratio of lipid to nucleic acid ranges from about 1 nmol to about 25 nmol lipid per 1 μg nucleic acid.

4. The method of claims 2 or 3, wherein the polycation:nucleic acid ratio is about 0.01 μg to about 100 μg polycation to 1 μg nucleic acid.

5. The method of claim 1, wherein the cationic liposomes comprise a cationic lipid and a neutral phospholipid.

6. The complex of claim 5, wherein said polycation is poly-L-lysine having a molecular weight of about 300 to about 200,000, said cationic lipid is 3β|N-(N',N'- dimethylaminoethane)carbamoyl|cholesterol and the neutral phospholipid is dioleoylphosphatidlyethanolamine.

7. The method of claim 1, wherein said complex has an average diameter less than about 400 nm.

8. A noncovalent nucleic acid lipid/polycation complex having a net positive charge at pH 6.0–8.0; said complex being produced by mixing cationic liposomes with polycation and nucleic acid in a ratio of nucleic acid to lipid to polycation which results in the production of said complex, said polycation being selected from the group consisting of polyarginine, polyornithine, protamines, polylysine, polybrene (hexadimethrine bromide), histone, cationic dendrimer, spermine, spermidine and synthetic polypeptides derived from SV40 large T antigen and which synthetic polypeptides have excess positive charges and represent a nuclear localization signal.

9. The complex of claim 8, wherein the ratio of lipid to nucleic acid ranges from about 0.1 nmol to 200 nmol lipid per 1 µg nucleic acid.

10. The complex of claim 9, wherein the ratio of lipid to nucleic acid ranges from about 1 nmol to about 25 nmol lipid per 1 µg nucleic acid.

11. The complex of claims 9 or 10, wherein the polycation:nucleic acid ratio is about 0.01 µg to about 100 µg polycation to 1 µg nucleic acid.

12. The complex of claim 8, wherein the cationic liposomes comprise a cationic lipid and a neutral phospholipid.

13. The complex of claim 12, wherein said polycation is poly-L-lysine having a molecular weight of about 300 to 200,000, said cationic lipid is 3β|N-(N',N'-dimethylaminoethane)carbamoyl|cholesterol and said neutral phospholipid is dioleoylphosphatidlyethanolamine.

14. A pharmaceutical composition comprising the complex of claim 8.

15. A method for delivering nucleic acid to cells, said method comprising contacting the cells with the complex of claim 8.

16. The method of claim 15, wherein the cells are contacted with said complex in vivo.

17. The complex of claim 8, wherein the complex has an average diameter less than about 400 nmn.

18. The method of claim 1, wherein the nucleic acid is added to a mixture of cationic liposomes and polycation.

19. The method of claim 18, wherein said method further comprises the stop of purifying said complexes by a method selected from the group consisting of centrifugation, chromatography, filtration and phase partition.

20. The method of claim 1, wherein said method further comprises the step of purifying said complexes by a method selected from the group consisting of centrifugation, chromatography, filtration and phase partition.

21. The complex of claim 8, wherein said complex is substantially free of uncomplexed nucleic acid, liposomes and polycation.

* * * * *

UNITED STATES PATENT AND TRADEMARK OFFICE

CERTIFICATE OF CORRECTION

PATENT NO. : 5,795,587

DATED : August 18, 1998

INVENTOR(S) : Xiang GAO and Leaf HUANG

It is certified that error appears in the above-identified patent and that said Letters Patent is hereby corrected as shown below:

In Column 1, line 4, please insert:

--STATEMENT OF RIGHTS TO INVENTIONS MADE UNDER
FEDERALLY SPONSORED RESEARCH

This invention was made with Government support under Grant No. DK44935, awarded by the National Institutes of Health. The Government has certain rights in this invention."--

Signed and Sealed this

Seventeenth Day of April, 2001

Attest:

NICHOLAS P. GODICI

Attesting Officer     Acting Director of the United States Patent and Trademark Office

(12) EX PARTE REEXAMINATION CERTIFICATE (9753rd)
United States Patent
Gao et al.

(10) Number: US 5,795,587 C1
(45) Certificate Issued: Jul. 17, 2013

(54) STABLE LIPID-COMPRISING DRUG DELIVERY COMPLEXES AND METHODS FOR THEIR PRODUCTION

(75) Inventors: Xiang Gao, Pittsburgh, PA (US); Leaf Huang, Wexford, PA (US)

(73) Assignee: National Institute of Health (NIH), U.S. Dept. of Health and Human Services (DHHS), Bethesda, MD (US)

Reexamination Request:
No. 90/012,280, May 3, 2012

Reexamination Certificate for:
Patent No.: 5,795,587
Issued: Aug. 18, 1998
Appl. No.: 08/376,701
Filed: Jan. 23, 1995

Certificate of Correction issued Apr. 17, 2001

(51) Int. Cl.
*C12N 15/87* (2006.01)
*C12N 15/88* (2006.01)
*A61K 9/127* (2006.01)
*A61K 48/00* (2006.01)

(52) U.S. Cl.
CPC .............. *A61K 9/1272* (2013.01); *C12N 15/88* (2013.01)

USPC ........................................................... 424/450

(58) Field of Classification Search
None
See application file for complete search history.

(56) References Cited

To view the complete listing of prior art documents cited during the proceeding for Reexamination Control Number 90/012,280, please refer to the USPTO's public Patent Application Information Retrieval (PAIR) system under the Display References tab.

*Primary Examiner* — Evelyn Huang

(57) ABSTRACT

Novel stable, concentrated, biologically active and ready-to-use lipid-comprising drug delivery complexes and methods for their production are described. The biological activity of the complexes produced are comparable to the formulations prepared according to the prior art admixture method and upon purification, the complexes produced by the method of this invention are 50 to 500 fold more concentrated than the components of the complexes formed by admixture. The method described herein provides for the large scale production of lipid-comprising drug delivery systems useful for gene therapy and other applications.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 18 and 19 are cancelled.

Claims 1 and 8 are determined to be patentable as amended.

Claims 2-5, 7, 9-12, 14-17 and 20-21, dependent on an amended claim, are determined to be patentable.

Claims 6 and 13 were not reexamined.

1. A method for producing noncovalent nucleic acid/lipid/polycation complexes having a net positive charge at about pH 6.0-8.0, said method comprising mixing said nucleic acid with cationic liposomes and polycation in a ratio of nucleic acid to lipid to polycation which results in the production of said complexes, said polycation being selected from the group consisting of polyarginine, polyornithine, protamines, polylysine, polybrene (hexadimethrine bromide), histone, cationic dendrimer, spermine, spermidine and synthetic polypeptides derived from SV40 large T antigen, and which synthetic polypeptides have excess positive charges and represent a nuclear localization signal, *and wherein said nucleic acid is added to a mixture of said cationic liposomes and said polycation*.

8. A noncovalent nucleic acid lipid/polycation complex having a net positive charge at pH 6.0-8.0; said complex being produced by mixing cationic liposomes with polycation and nucleic acid in a ratio of nucleic acid to lipid to polycation which results in the production of said complex, said polycation being selected from the group consisting of polyarginine, polyornithine, protamines, polylysine, polybrene (hexadimethrine bromide), histone, cationic dendrimer, spermine, spermidine and synthetic polypeptides derived from SV40 large T antigen and which synthetic polypeptides have excess positive charges and represent a nuclear localization signal, *and wherein said nucleic acid is added to a mixture of said cationic liposomes and said polycation*.

* * * * *